(12) United States Patent
Kolb et al.

(10) Patent No.: US 7,166,111 B2
(45) Date of Patent: Jan. 23, 2007

(54) SPINAL PLATE AND DRILL GUIDE

(75) Inventors: Eric D. Kolb, Milton, MA (US); Jonathan Fanger, Fall River, MA (US)

(73) Assignee: Depuy Spine, Inc., Raynham, MA (US)

( * ) Notice: Subject to any disclaimer, the term of this patent is extended or adjusted under 35 U.S.C. 154(b) by 0 days.

(21) Appl. No.: 10/904,987

(22) Filed: Dec. 8, 2004

(65) Prior Publication Data
US 2006/0122607 A1    Jun. 8, 2006

(51) Int. Cl.
*A61B 17/70* (2006.01)
(52) U.S. Cl. ...................................................... 606/96
(58) Field of Classification Search ................ 606/96, 606/104
See application file for complete search history.

(56) References Cited

U.S. PATENT DOCUMENTS

| | | | | |
|---|---|---|---|---|
| 4,686,972 A | * | 8/1987 | Kurland ..................... | 606/96 |
| 5,030,219 A | * | 7/1991 | Matsen et al. .............. | 606/53 |
| 5,180,381 A | | 1/1993 | Aust et al. | |
| 5,423,826 A | | 6/1995 | Coates et al. | |
| 5,603,713 A | | 2/1997 | Aust et al. | |
| 5,700,266 A | * | 12/1997 | Harryman, II .............. | 606/80 |
| 5,746,743 A | * | 5/1998 | Greenberg .................. | 606/96 |
| 5,851,207 A | | 12/1998 | Cesarone | |
| 6,200,322 B1 | * | 3/2001 | Branch et al. ............... | 606/96 |
| 6,342,057 B1 | | 1/2002 | Brace et al. | |
| 6,379,364 B1 | | 4/2002 | Brace et al. | |
| 6,565,571 B1 | * | 5/2003 | Jackowski et al. .......... | 606/69 |

(Continued)

FOREIGN PATENT DOCUMENTS

| | | |
|---|---|---|
| WO | WO 03/007826 A1 | 1/2003 |
| WO | WO 03/024344 | 3/2003 |

OTHER PUBLICATIONS

"Biomechanical Evaluation of a Newly Developed Monocortical Expansion Screw for the in the Anterior Internal Fixation of the Cervical Spine—In-Vitro Comparison With 2 Established Internal Fixation Systems," Richter, M. et al., Department of Orthopedics, University of Ulm, Germany, Feb. 1, 1999.

(Continued)

*Primary Examiner*—Eduardo C Robert
*Assistant Examiner*—Thomas Sweet

(57) ABSTRACT

Bone plates and bone plate systems are provided in which a bone plate includes first and second longitudinally extending rails, with a plurality of bone screw holes formed therein. At least one transverse strut connects the first and second longitudinally extending rails, each of the at least one transverse struts being disposed between adjacent bone screw holes formed on the same longitudinally extending rail. The bone plate system can additionally include a plurality of bone screws adapted for placement within the bone screw holes and a guide device. The guide device can register with at least one bone screw hole of the bone plate by placement of an alignment element upon a portion of the bone plate external to one of the bone screw holes such that one of the bone screws can be installed in one of the bone screw holes of the plate through the guide barrel while the guide device is registered with at least one of the bone screw holes.

5 Claims, 11 Drawing Sheets

U.S. PATENT DOCUMENTS

| | | |
|---|---|---|
| 2002/0082606 A1 | 6/2002 | Suddaby |
| 2003/0233098 A1 | 12/2003 | Markworth |
| 2004/0015174 A1 | 1/2004 | Null et al. |
| 2004/0092947 A1* | 5/2004 | Foley .......................... 606/96 |
| 2004/0097925 A1 | 5/2004 | Boehm, Jr. et al. |
| 2004/0204717 A1* | 10/2004 | Fanger et al. ................. 606/96 |

OTHER PUBLICATIONS

AXIS Fixation System product brochure, Sofamor Danek, Memphis, TN, 1997.
DePuy ACE product line, DePuy Orthopaedics, Inc., 2004.
DOC Ventral Cervical Plate System, DePuy AcroMed Inc. product catalog, 2001.
SUMMIT Fixation System, DePuy AcroMed, Inc. product catalog, 2000.
Anderson, P, "The Tether Anterior Cervical Plating System," Surgical Dynamics.
Blackstone Anterior Cervical Plate, Blackstone Medical, Inc. product brochure.
SC-AcuFix, Spinal Concepts, Inc., Feb. 2000.

* cited by examiner

SPINAL PLATE AND DRILL GUIDE

FIELD OF THE INVENTION

The present invention relates to fixation devices used in orthopaedic and spinal surgery and particularly to bone fixation plates useful for positioning and immobilizing bone segments.

BACKGROUND

For a number of known reasons, bone fixation devices are useful for promoting proper healing of injured or damaged vertebral bone segments caused by trauma, tumor growth, or degenerative disc disease. The fixation devices immobilize the injured bone segments to ensure the proper growth of new osseous tissue between the damaged segments. These types of bone fixation devices often include internal bracing and instrumentation to stabilize the spinal column to facilitate the efficient healing of the damaged area without deformity or instability, while minimizing any immobilization and post-operative care of the patient.

One such device is an osteosynthesis plate, more commonly referred to as a bone fixation plate, that can be used to immobilize adjacent skeletal parts such as bones. Typically, the fixation plate is a rigid metal or polymeric plate positioned to span bones or bone segments that require immobilization with respect to one another. The plate is fastened to the respective bones, usually with bone screws, so that the plate remains in contact with the bones and fixes them in a desired position. Bone plates can be useful in providing the mechanical support necessary to keep vertebral bodies in proper position and bridge a weakened or diseased area such as when a disc, vertebral body or fragment has been removed.

Such plates have been used to immobilize a variety of bones, including vertebral bodies of the spine. These bone plate systems usually include a rigid bone plate having a plurality of screw openings. The openings are either holes or slots to allow for freedom of screw movement. The bone plate is placed against the damaged vertebral bodies and bone screws are used to secure the bone plate to the spine, usually with the bone screws being driven into the vertebral bodies. Exemplary systems are described in U.S. Pat. No. 6,159,213 to Rogozinski; U.S. Pat. No. 6,017,345 to Richelsoph; U.S. Pat. No. 5,676,666 to Oxland et al.; U.S. Pat. No. 5,616,144 to Yapp et al.; U.S. Pat. No. 5,549,612 to Yapp et al.; U.S. Pat. No. 5,261,910 to Warden et al.; and U.S. Pat. No. 4,696,290 to Steffee.

Despite the existence of these bone plate systems, there remains a need for a bone plate system that can provide increased visualization of a surgical site to facilitate alignment and implantation of bone plate. There is also a need for a bone plate system which enables convenient installation of a bone screw through a drill guide.

SUMMARY

Disclosed herein are bone plate systems including a bone plate having a unique geometry that renders the plate effective and convenient to install. In spinal plate applications, for example, the plate provides for enhanced visibility of the vertebral bodies on which they are mounted. The bone plate system also facilitates ease of installation. The bone plate is designed to enable the use of a guide device that can achieve a variety of trajectories while maintaining registration with a bone screw hole(s) during screw installation. As a result, the bone plate system facilitates optimized bone plate alignment, as well as proper and efficient placement of bone screws.

In one embodiment, a bone plate is provided that includes first and second longitudinally extending rails that are separated from each other at least at one of a superior and an inferior end of the bone plate. Each rail has a plurality of bone screw holes for receiving bone screws, and at least one transverse strut connects each of the rails. An outer sidewall of each of the rails has a curvature along at least a portion of its length adjacent to the bone screw holes that are formed at least at the superior and inferior ends of the plate. In one embodiment the curvature of the outer sidewall defines a circular arc, which can extend over at least approximately 45°, at least over approximately 90° or, in another embodiment, at least over approximately 145°.

In a further aspect, opposed bone screw holes formed on adjacent rails are separated by an open area in the plate. The open area can be formed, for example, by the placement of the transverse strut(s). The transverse strut(s) can be disposed between adjacent bone screw holes formed on the same longitudinally extending rail. In one embodiment, the bone plate is a single level plate having two bone screw holes formed in each rail and a single transverse strut. In another embodiment, the bone plate can be a multilevel plate that includes three or more bone screw holes in each rail and two or more transverse struts connecting the first and second rails with an open area positioned between the struts.

In a further embodiment, an implantable bone plate system is disclosed. The system includes a bone plate having first and second longitudinally extending rails, with a plurality of bone screw holes formed in each of the first and second longitudinally extending rails. At least one transverse strut can connect each of the first and second longitudinally extending rails and be disposed between adjacent bone screw holes formed on the same longitudinally extending rail. In addition, the system includes a plurality of bone screws and a guide device, such as a drill/screw guide, adapted for use with the bone plate. The guide device has a handle portion, a guide barrel, and at least one feature extending from a distal end of the guide barrel. The guide device is adapted to register with at least one bone screw hole of the bone plate by placement of the at least one feature upon a portion of the bone plate external to the bone screw hole such that a bone screw can be installed in the bone screw hole through the guide barrel while the guide device is registered with the bone screw hole.

In one aspect, at least one feature of the guide device is adapted to engage a curved outer sidewall of the at least one of the first and second longitudinally extending rails. For example, the at least one feature of the guide device can include one or more tabs having a shape corresponding to a curved outer side surface of the bone plate. The tab(s) can be spaced or configured to receive a portion of the bone plate, such as, for example one of the first and second longitudinally extending rails. In use, the guide can pivot while registered with the bone plate. In another embodiment, the drill guide can include two guide barrels and the guide device is adapted to register with two bone screw holes.

In yet another embodiment, a single barrel guide device is disclosed. The guide device includes a handle and a guide barrel portion extending from the handle. In addition, one or more features extend from a distal end of the guide barrel. The feature(s) are adapted to engage a single bone screw hole on a bone plate such that the feature(s) engage a portion of the bone plate adjacent to and external to the bone screw hole such that the guide barrel is adapted to receive and guide an instrument and/or implant (e.g., a bone screw) through the bone screw hole.

BRIEF DESCRIPTION OF THE DRAWINGS

The invention can be more fully understood from the following detailed description taken in conjunction with the accompanying drawings, in which.

DETAILED DESCRIPTION OF THE EXEMPLARY EMBODIMENTS

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The following exemplary embodiments are described herein with reference to bone plates used to span and immobilize adjacent vertebral bodies in spinal fixation techniques. However, it is understood that the bone plate systems described herein may be applicable to the fixation of any type of adjacent bones or bone segments.

In general, disclosed herein is a bone plate defined by first and second longitudinally extending rails, each having a plurality of bone screw holes formed therein. The rails are separated from each other at least at one of a superior and an inferior end of the bone plate. In one embodiment at least one transverse strut that is positioned between adjacent bone screw holes formed on the longitudinally extending rails connects the adjacent rails.

The plate illustrated and described in the exemplary embodiments is particularly well suited for placement in the anterior cervical region of the spine. The plate can be in the form of a single level plate, which spans two adjacent vertebral bodies, or a multilevel plate that spans three or more adjacent vertebral bodies.

Figure 1:
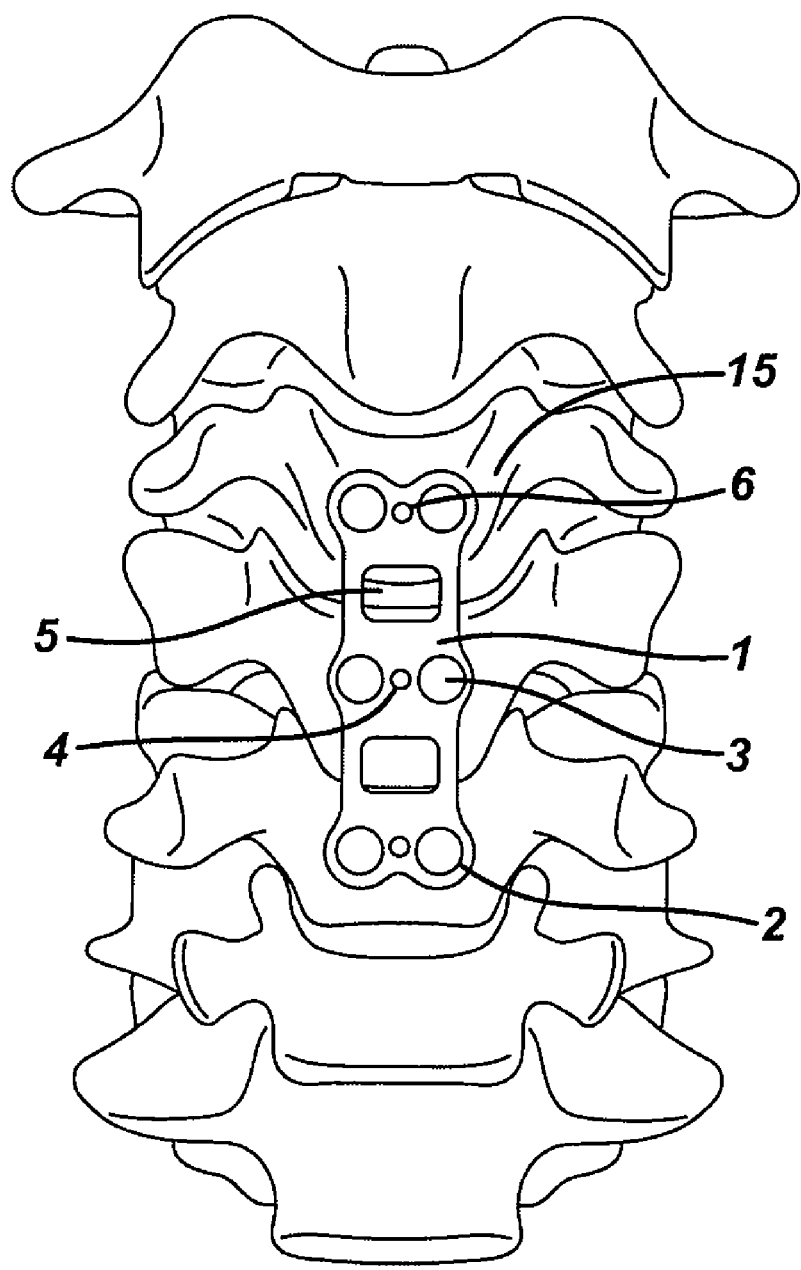
FIG. 1 is a prior art fixation device mounted on a spinal column.
Figure 2:
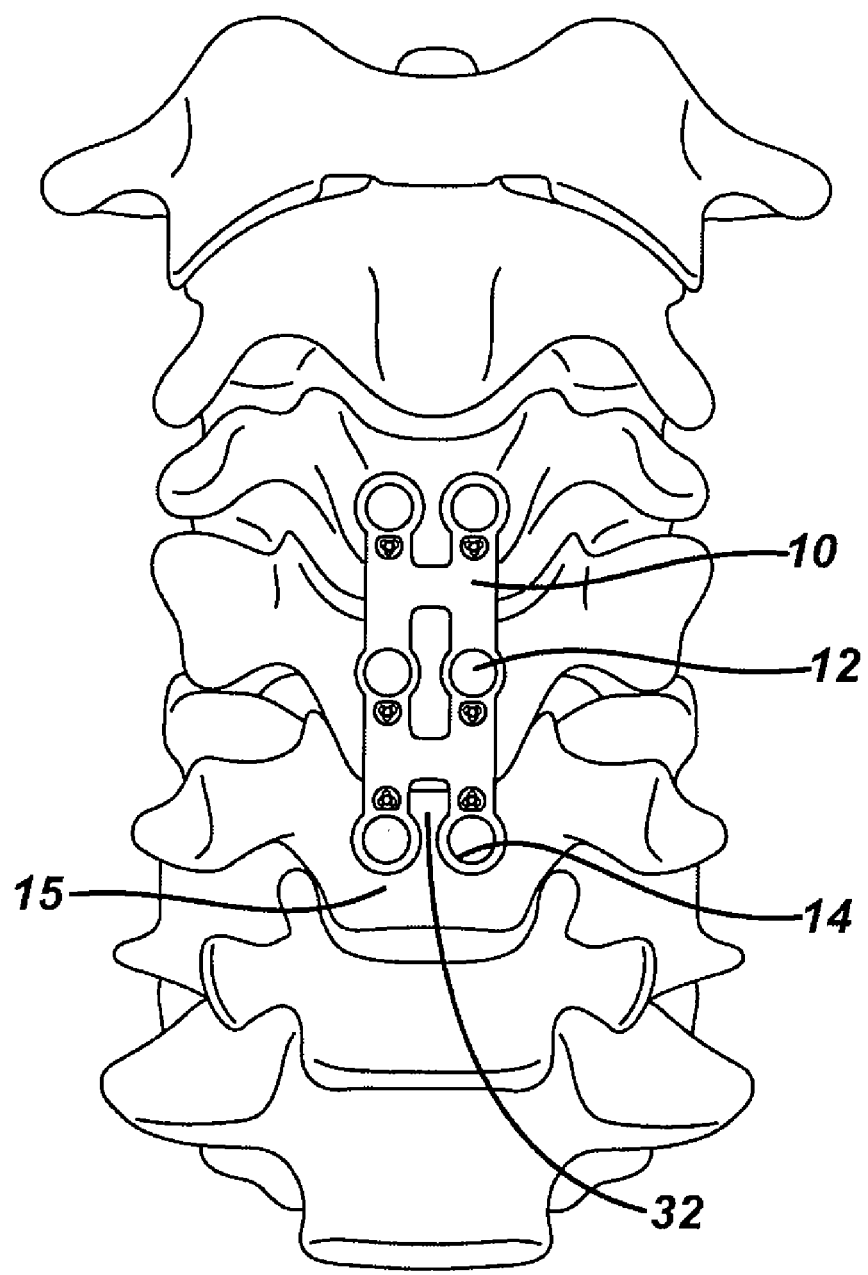
FIG. 2 shows a top view of one embodiment of a bone plate encompassed by the invention mounted on a spinal column.

FIG. 1 illustrates a previously known bone plate 1 having a plurality of bone screw holes 2 and bone screws 3. The bone plate of FIG. 1 has substantially closed regions 4 between laterally opposed bone screw holes and visualization windows 5 disposed between the closed regions. Substantially closed regions 4 obscure the vertebral bodies 15 while windows 5 allow some visibility of the intervertebral space. The plate 1 also includes fixation pin-receiving holes 6. In contrast, disclosed herein is plate which, as illustrated in FIG. 2 mounted upon an anterior cervical surface of a spine, has open spaces 32 between laterally opposed pairs of bone screw holes 14, thereby providing enhanced visualization of the vertebral bodies 15 on which the plate is to be mounted with bone screws 12.

FIGS. 2 through 6 illustrate certain exemplary embodiments of a bone plate 10 as disclosed herein. In general, the bone plate 10 is formed of first and second longitudinally extending rails 16, 18 that are connected to each other by transverse struts 20. Each plate has a bone contacting surface (not shown) and an opposed, non-bone contacting surface 22. A plurality of bone screw holes 14 are formed in each rail 16, 18, extending through the plate from the non-bone contacting surface 22 to the bone contacting surface.

Figure 4:
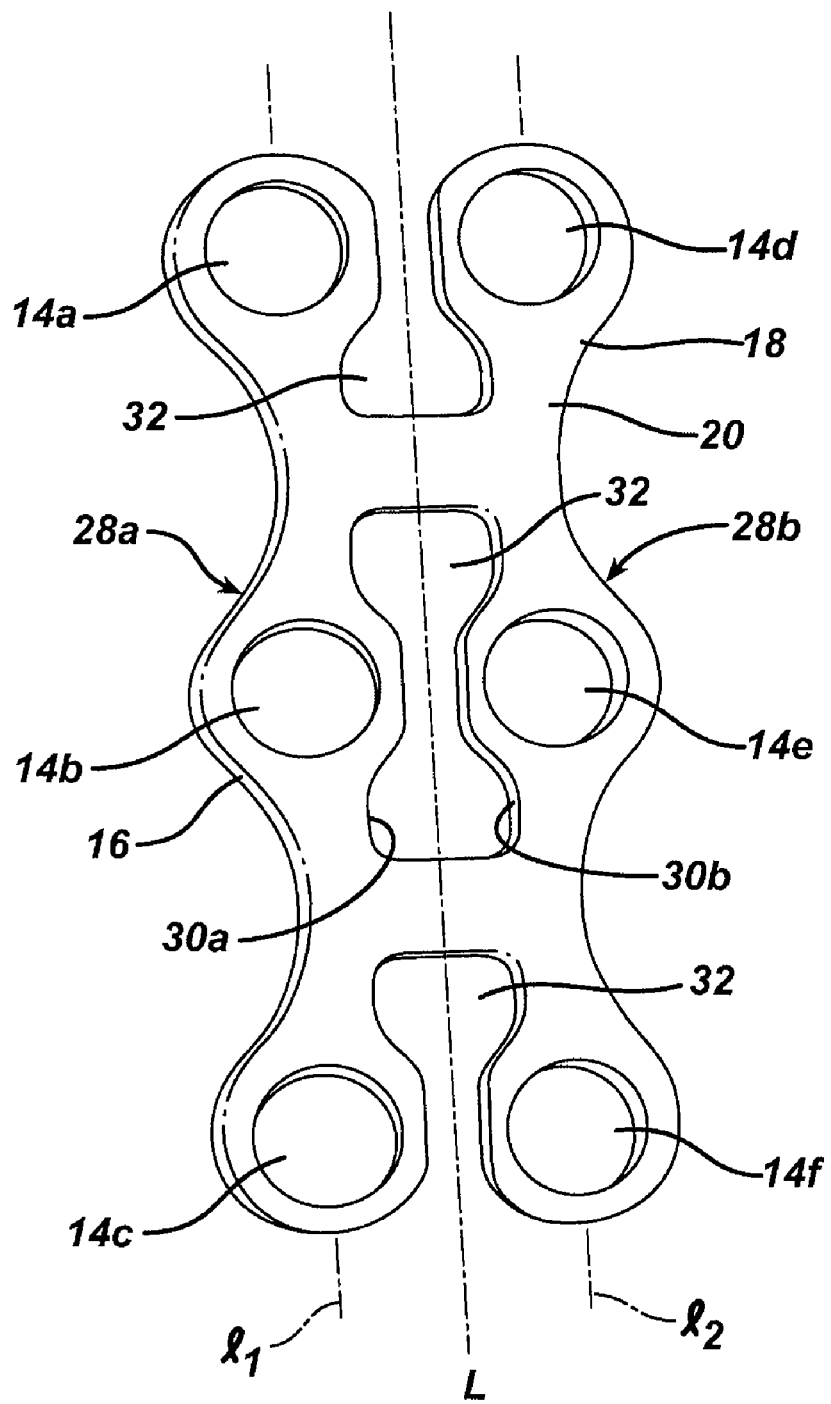
FIG. 4 is a perspective view of yet another embodiment of a bone plate encompassed by the invention.

The plate 10, and each rail 16, 18, has a superior end 24, a middle portion 25, and an inferior end 26. A longitudinal axis L (FIG. 4) extends through the plate from superior end 24 to inferior end 26, with rails 16, 18 extending substantially parallel to each other and to axis L. Each rail 16, 18 also has a longitudinal axis 11, 12 (FIG. 4). Further, rails 16, 18 have outer sidewalls 28a, 28b, which define the outer edge of the plate, and inner sidewalls 30a, 30b, which are opposed to one another.

Bone screw holes 14a–f (FIG. 4) are positioned along the length of the rails for receiving bone screws to implant the plate within bone. In one aspect, the bone screw holes are positioned along the longitudinal axes 11, 12 of rails 16, 18 and are spaced such that adjacent bone screw holes on the same rail (e.g., holes 14a, 14b and 14b, 14c) will be positioned adjacent to different vertebral bodies when the bone plate is implanted within a patient. In the embodiments illustrated in FIGS. 2–6, bone plate 10 is a two level plate having three bone screw holes 14 positioned on each rail 16, 18, thus forming three opposed pairs (14a, 14d; 14b, 14e; and 14c, 14f) of bone screw holes. Other types of plates are also contemplated, including, for example, a single level plate having two bone screw holes in each rail and two pairs of opposed bone screw holes. In addition, other plates, such as three or more level plates are also contemplated.

FIGS. 2–6 illustrate open spaces 32 that are disposed between rails 16, 18 and opposed pairs of bone screw holes 14 in plate 10. The open spaces 32, as noted above, provide enhanced visibility of the vertebral bodies onto which plate 10 is to be mounted. In particular, the open spaces 32 can be useful to ensure proper alignment of the plate on the vertebral bodies. For example, the open spaces 32 can allow a midline view of the vertebrae to facilitate a midline alignment of plate 10 on the vertebral bodies.

The open spaces 32 can, in part, be formed by the positioning of struts 20. The struts 20, for example, can be positioned at any location between adjacent bone screw holes 14 on each longitudinal rail 16, 18. That is, struts 20 can be positioned at any location between a first imaginary line formed between inferior edges of superior opposed bone screw holes and a second imaginary line formed between superior edges of adjacent inferior opposed bone screw holes.

In one embodiment, transverse struts 20 are positioned substantially at the midpoint between adjacent bone screw holes 14 on rails 16, 18 to maximize the view of vertebral bodies. For example, FIGS. 2 through 5 illustrate struts 20 positioned substantially at the midpoint between adjacent bone screw holes 14 such that when bone plate 10 is placed on a spinal column, struts 20 will be substantially aligned with the disc space between vertebral bodies.

Figure 6:
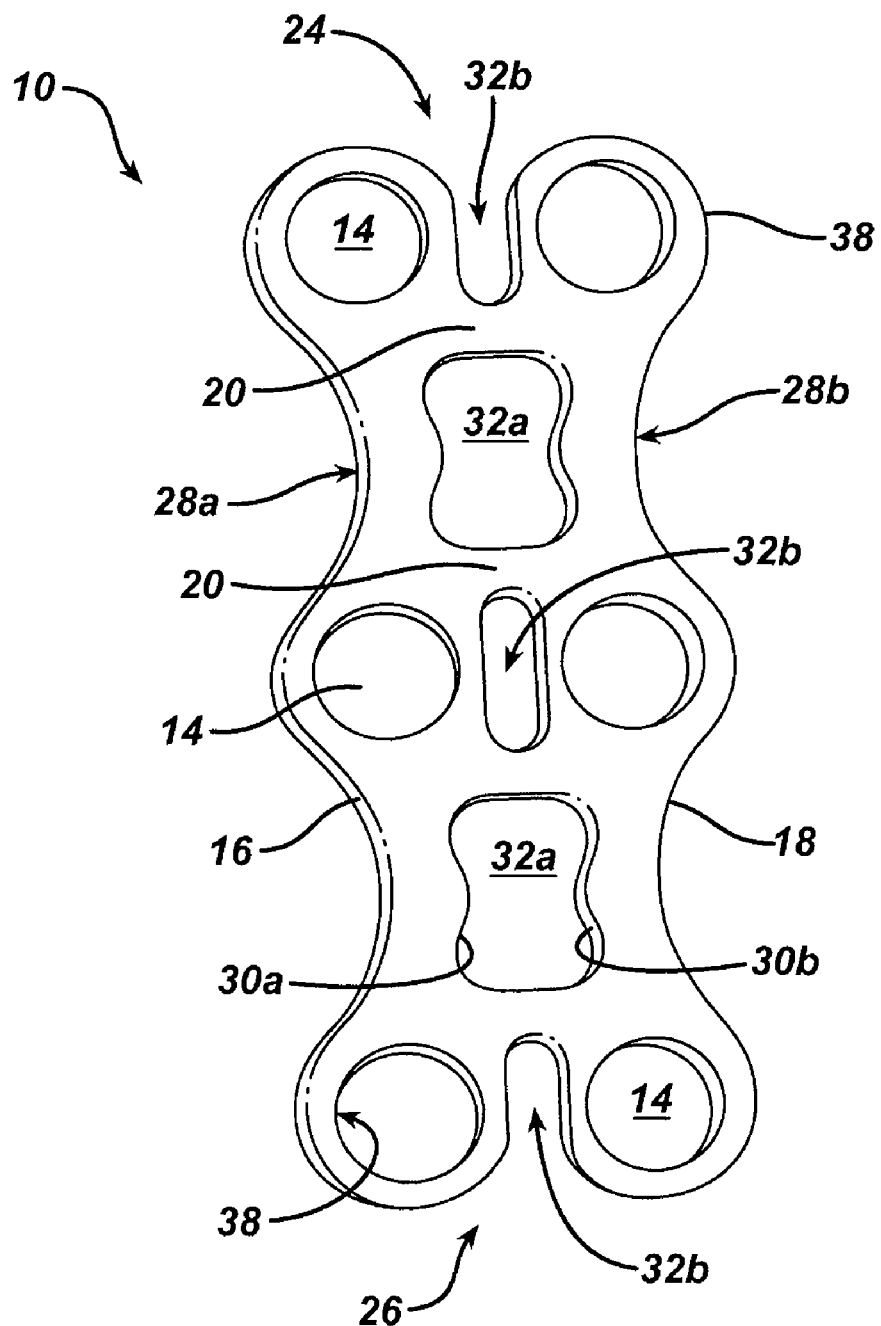
FIG. 6 is a perspective view of a further embodiment of a bone plate encompassed by the invention.

In an alternative embodiment, struts 20 can be positioned so as to be offset from the midpoint between adjacent bone screw holes such that a view of both the vertebral body and the disc space is provided. FIG. 6 illustrates one such exemplary embodiment in which struts 20 are positioned immediately adjacent to bone screw holes 14 such that two struts are positioned between each of the substantially adjacent bone screw holes 14 on rails 16, 18. As shown, a window 32a is located between each pair of adjacent struts 20 and corresponds to the location of the disc, while a window 32b is positioned between opposed pairs of bone screw holes and corresponds to the location of vertebral bodies. This plate configuration allows a surgeon at least a partial view of the disc space, as well as the vertebral bodies. For example, the bone plate 10 of FIG. 6 would enable a surgeon to view a graft, or another interbody fusion device, inserted between vertebral bodies.

Regardless where struts 20 are positioned, an open space between opposed bone screw holes 14 on different rails 16, 18 is created at least at one of the superior and inferior ends 24, 26. As shown in FIGS. 2 through 6, rails 16, 18 are separated from one another at both the superior and inferior ends 24, 26, as well as, between the bone screw holes disposed at a middle portion 25 of the plate.

Rails 16, 18, of bone plate 10, can be formed in a variety of shapes. In one embodiment, illustrated in FIGS. 2 and 3, the rails 16, 18 are similarly shaped. In another embodiment, illustrated in FIGS. 4 through 6, the rails, 16, 18 are mirror images of one another.

The shape of rails 16, 18 can also include variations in width along the longitudinal axes of the rails. In one embodiment, the width of rails 16, 18 is greatest across bone screw holes 14 to provide support to bone screws 12. For example, rails 16, 18 can have shapes, for example convex curvatures, that provide additional width across bone screw hole 14 and narrower widths between the bone screw holes.

Figure 3:
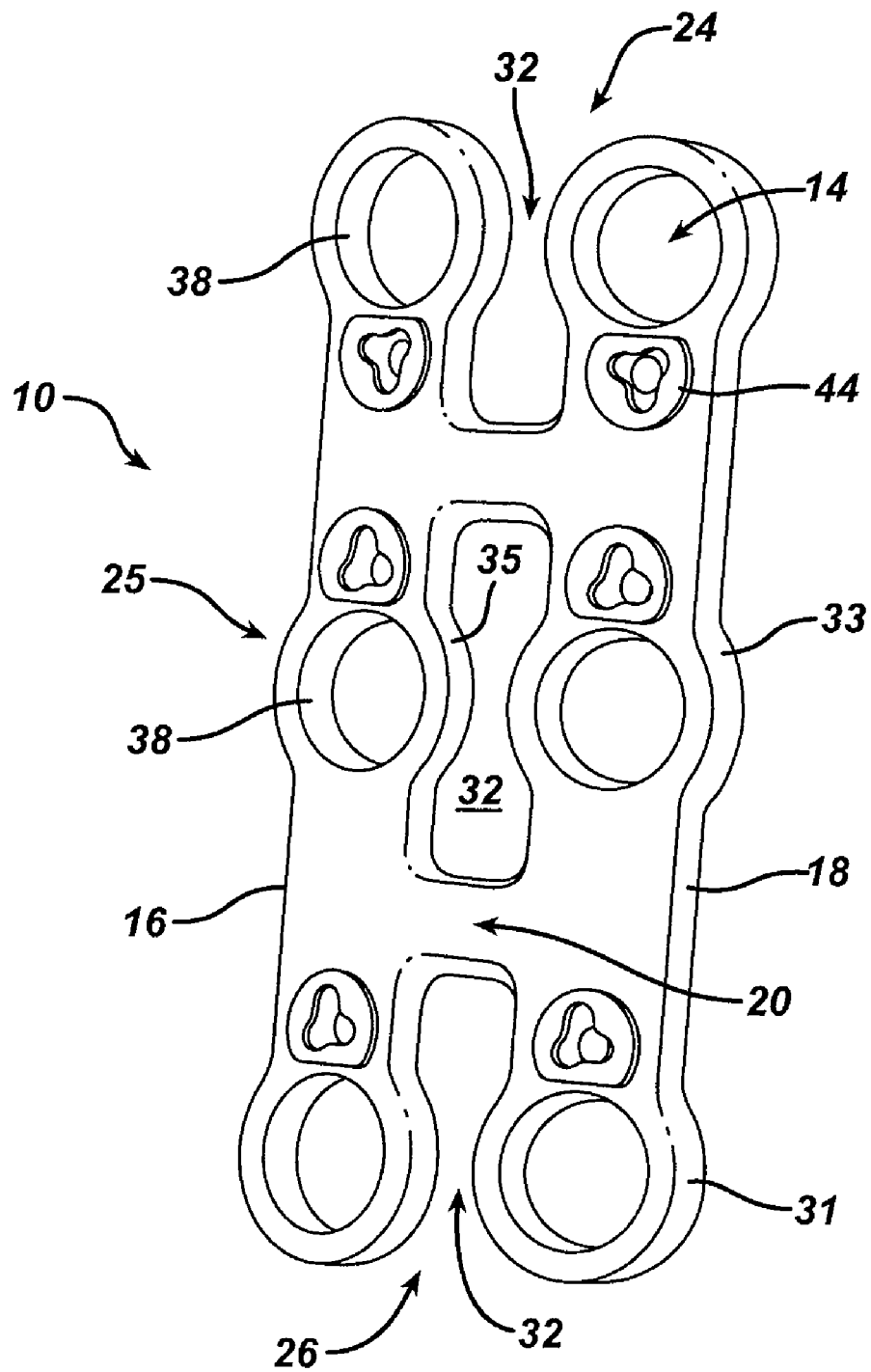
FIG. 3 is a perspective view of another embodiment of a bone plate encompassed by the invention.

Bone plate 10 illustrated in FIGS. 2 and 3 includes a width that varies along the longitudinal axis of the plate, and the outer sidewalls 28a, 28b and inner sidewalls 30a, 30b of the plate are substantially linear, except adjacent to bone screw holes 14. The outer and inner sidewalls of the plate surrounding bone screw holes 14 have a curved shape. In particular, the outer and inner sidewalls adjacent bone screw holes 14 at superior 24 and inferior 26 ends of the plate can follow a curvature that matches at least a portion of the curvature of inner wall 38 that defines the bone screw holes 14. The outer sidewall of the bone plate adjacent the bone screw holes at the superior 24 and inferior 26 ends of the plate thus can follow a curvature that is at least partially circular. In one embodiment, the plate adjacent the bone screw holes at the superior 24 and inferior 26 ends of the plate includes a curved outer sidewall segment 31 that defines a substantially circular arc extending over at least approximately 200°, and more preferably over at least approximately 270°.

Outer and inner sidewall segments 33, 35 surrounding the bone screw holes 14 in the middle portion 25 of the plate in the embodiment of FIGS. 2 and 3 are likewise curved. Segments 33, 35 can have a curvature complementary to a corresponding segment of inner wall 38 that defines the bone screw holes 14. In one embodiment, segments 33, 35 each define a substantially circular arc that extends over at least approximately 45°.

Figure 5:
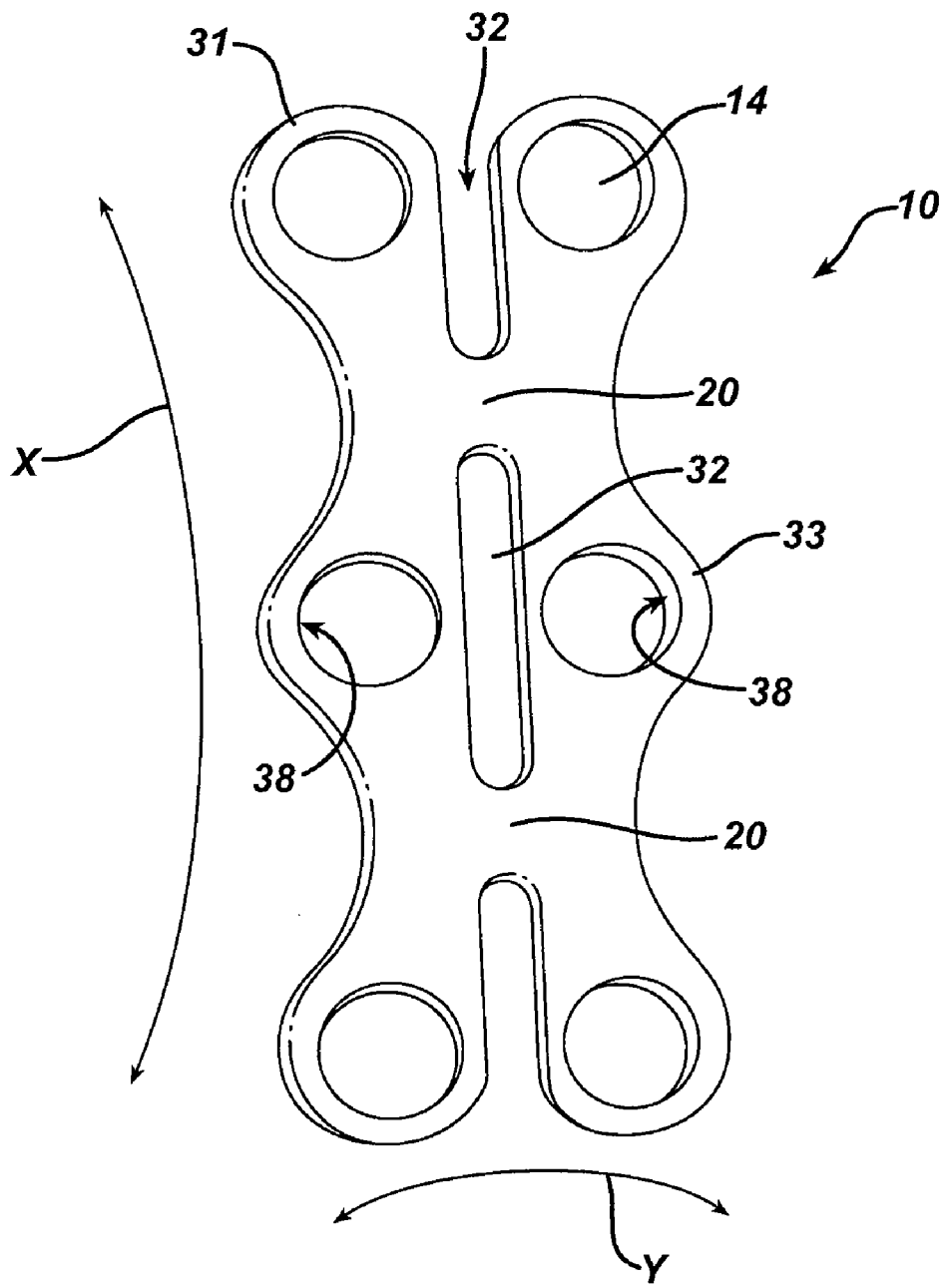
FIG. 5 is a perspective view of still another embodiment of a bone plate encompassed by the invention.

FIGS. 2 and 3 illustrate a bone screw hole within a symmetrically shaped perimeter. That is, laterally opposed sides of the bone screw holes all have the same shape (e.g., substantially circular). FIGS. 4 through 6, on the other hand, illustrate embodiments in which the bone screw holes have asymmetrical laterally opposed sides, as discussed below.

The outer sidewalls 28a, 28b of the rails 16, 18 in FIGS. 4 through 6 have a generally non-linear, undulating shape along the length of the bone plate, thereby providing additional width across the bone screw holes while minimizing the plate size. For example, the plate illustrated in FIG. 5 includes outer sidewalls 28a, 28b that are bowed or curved inwardly along the outer sides 28a, 28b between adjacent bone screw holes 14 formed on the same rail, while the inner sides 30a, 30b are substantially linear. The linear portion can be useful to mate with a guide device and to limit rotation of the guide device to a single plane, as explained below, and to facilitate engagement with a fixation pin or Caspar pin.

FIGS. 4 and 6 illustrate further embodiments of bone plate 10 in which the outer sidewalls 28a, 28b of rails 16, 18, similar to those of FIG. 5, are bowed or curved inwardly between adjacent bone screw holes. The inner sidewalls are bowed or curved outwardly adjacent to struts 20 and are substantially linear between opposed pairs of bone screw holes 14. The resulting bone plates have a generally hourglass-shaped viewing window(s) 32 between inner sides 30a, 30b that provides a surgeon with maximum visualization of the vertebral midline.

In one aspect of the plates illustrated in FIGS. 4 through 6, an outer sidewall segment 31 (FIG. 5) adjacent to the bone screw holes at the superior and inferior ends of the plate has a curvature that substantially matches the curvature of an inner wall 38 that defines the bone screw holes. The curvature of outer sidewall segment 31 (FIG. 5) at the superior and/or inferior end of bone plate 10 may, in one embodiment, define a substantially circular arc that extends over at least approximately 145° and more preferably over at least approximately 180°.

The outer wall segments adjacent the bone screw holes 14 in the middle portion 25 of plate 10 can likewise have a curvature that matches a corresponding segment of inner wall 38 that defines bone screw holes 14. In one embodiment, outer wall segment 33 (FIG. 5) defines a substantially circular arc that extends over at least approximately 45°.

The dual rail configuration of the bone plate, in addition to providing midline viewing windows, can facilitate registration of a surgical tool (e.g., a guide device) with a portion of the bone plate (i.e., a bone screw hole). To further assist with mating a tool to bone plate 10, the non bone-contacting surface 22 of the bone plate and/or sidewalls, can have a surface topography that is substantially spherical or radiused. Such a spherical or radiused surface enables a guide device, for example, to be mated to a bone screw hole in such a way that the guide trajectory can be adjusted (e.g., pivoted) while maintaining registration of the guide with the bone screw hole.

Bone plate 10 disclosed herein can have features that facilitate mounting of bone plate 10 on a vertebral column, such as, for example, a preformed curvature that is complementary to the vertebrae upon which the plate is to be mounted. For example, the bone-contacting surface of the exemplary plate 10 can have a longitudinal curve X (FIG. 5) that approximates the lordotic curvature of the vertebrae upon which the plate is to be mounted. As shown in FIG. 5, the exemplary plate has a longitudinal curve X that extends in the sagital plane (i.e., in the superior-inferior direction) and that has constant radius along the length of the plate 10. Alternatively, the plate 10 may comprise a plurality of longitudinal segments that are configured to collectively provide the plate with a longitudinal curvature that approximates the lordotic curvature of the vertebrae. For example, one or more of the longitudinal segments may have a longitudinal curvature or may be oriented at angle relative to the other longitudinal segments.

While the exemplary plate 10 may be curved only along longitudinal axis L, in another embodiment, plate 10 can also include a transverse curve Y (FIG. 5) that approximates the transverse curvature of the vertebrae upon which the plate is to be mounted. The plate 10 may have a transverse curvature along the length of the plate 10 or along discrete longitudinal segments of the plate. For example, the middle portion 25 of the exemplary plate may have a transverse curvature that approximates the transverse curvature of the vertebrae. Alternatively, the superior end 24 and/or the inferior end 26 may have a different transverse curvature.

In addition, or as an alternative, bone plate 10 can be manipulated by a surgeon and bent to meet a desired curvature. In one embodiment, rails 16, 18 are independently bendable along their longitudinal axes ($I_1$, $I_2$). Further, a surgeon can bend plate 12 along transverse axis X. To facilitate bending, the plate may include bend zones (not shown), which are thinner areas of the plate that contribute to ease of bending.

Figure 7:
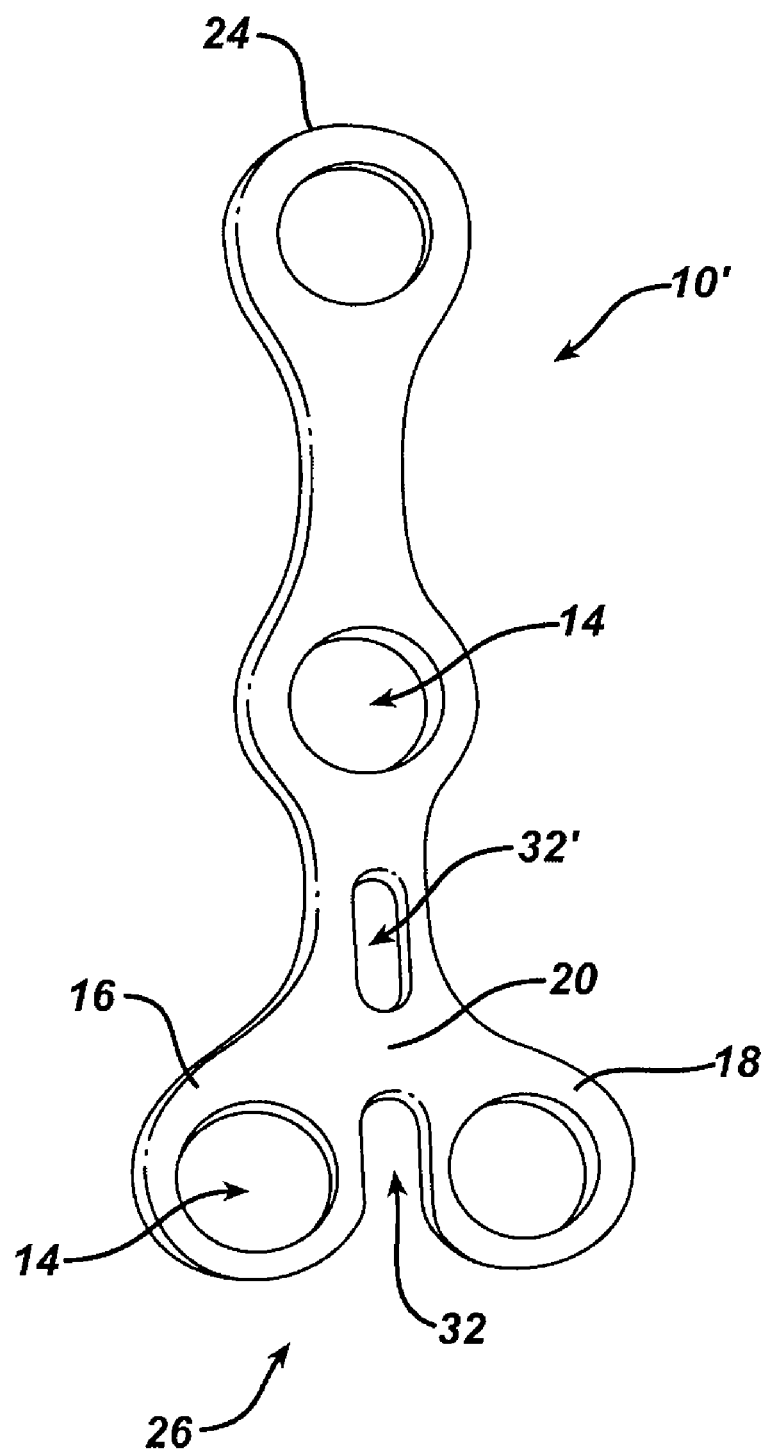
FIG. 7 is a top view of another embodiment of a bone plate encompassed by the invention.

In an alternative embodiment of the bone plate disclosed herein, one or more portions of the bone plate (e.g., inferior, middle, superior) include a dual rail configuration while the other portion(s) has a solid body. For example, FIG. 7 illustrates a bone plate 10' having a single elongate body at the superior end 24 and rails 16, 18 at the inferior end. Rails 16, 18 provide an open space 32 between opposed bone screw holes at the inferior end 26. This configuration provides an open area 32 between opposed bone screw holes 14 at the inferior end 26 of the plate. The inferior end 26 can optionally include a strut 20 that connects the rails and/or a window 32' for the viewing intervertebral space. The inferior end 26 of plate 10' in FIG. 7 can further include the other features of rails 16, 18 such as, for example, a curved outer sidewall as described above.

One skilled in the art will appreciate that the other regions of the plate 10 can have a variety of configurations. However, in one embodiment, the superior end bone plate 10 illustrated in FIG. 7 includes a single bone screw per vertebral body and can have features of the bone plate described in the U.S. patent application entitled "Spinal Plate System and Method of Use," filed Nov. 16, 2004, the disclosure of which is hereby incorporated by reference in it entirety.

Figure 8A:
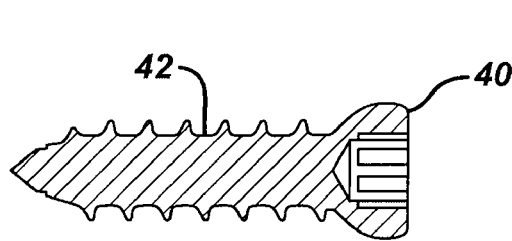
FIG. 8A is a side view of a bone screw that can be used with the bone plate disclosed herein.
Figure 8B:
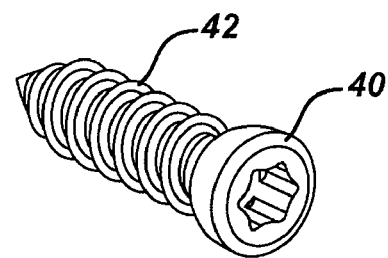
FIG. 8B is a perspective view of the bone screw of FIG. 8A.

In another embodiment, a bone plate system, including bone plate 10 and bone screws 12, is disclosed. FIGS. 8A and 8B illustrate an exemplary bone screw 12 that has a proximal head portion 40 and a distal threaded shank 42. Head 40 can be shaped and dimensioned to sit within bone screw hole 14 when implanted into bone to fix bone plate 10 in position. One skilled in the art will that bone screw 12 is exemplary and that a variety of other bone screws can be used with the bone plate system.

Figure 8C:
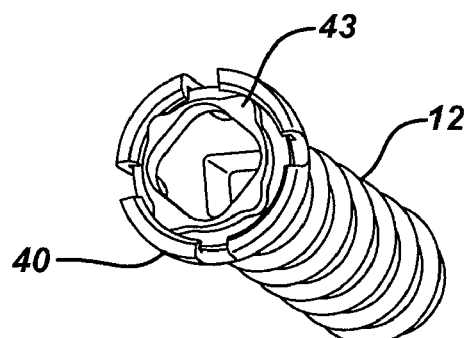
FIG. 8C is perspective view of another embodiment of a bone screw that can be used with the bone plate disclosed herein.
Figure 8D:
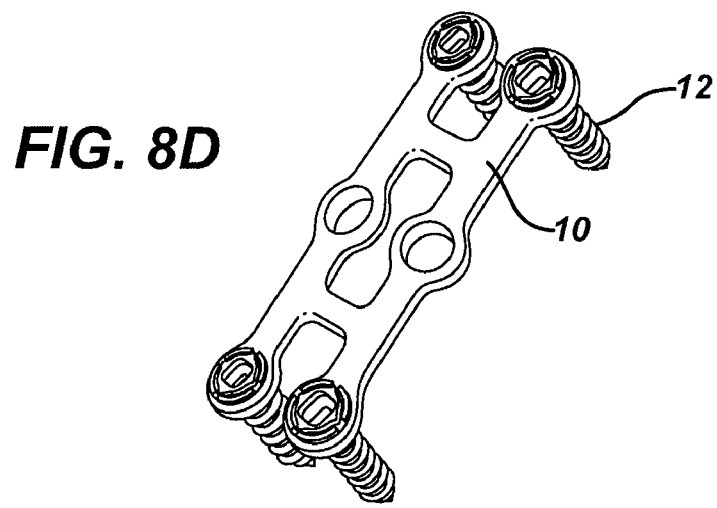
FIG. 8D is a perspective view of the bone screw of FIG. 8C positioned within bone screw holes of the bone plate disclosed herein.

Once bone screw 12 is implanted through bone plate 10, a surgeon can lock the bone screws to bone plate 10 to prevent screw backout. For example, the various embodiments of the spinal plates disclosed herein can include a locking or retaining mechanism for locking the bone screw to the bone plate and preventing bone screw backout. In one embodiment, the locking mechanism can be integrated into the screw head, as described in a U.S. Patent filed concurrently herewith and entitled "Locking Bone Screw and Spinal Plate System" of Gorhan et al., which is incorporated by reference herein in its entirety. For example, FIG. 8C illustrates bone screw 12 with an integrated locking cam 43 rotatably positioned within bone screw head 40 and FIG. 8D illustrates the bone screw of FIG. 8C positioned within bone plate 10. In use, bone screw 12 can be seated in bone screw holes 14 as shown in FIG. 8D and the locking cam 43 can be rotated to provide bone screw backout resistance.

In another embodiment, the locking mechanism can be integrated onto the surface of the plate. The integrated locking mechanism can be, for example, a cam that is rotatable between an unlocked position and a locked position, in which the cam is forced against the head of the bone screw to provide bone screw backout resistance. For example, FIG. 3 illustrates cam 44 rotatably positioned adjacent to bone screw hole 14 of bone plate 10. Other exemplary cam-type locking mechanisms are described in U.S. Pat. No. 5,549,612 of Yapp et al. entitled "Osteosynthesis Plate System," which is also incorporated by reference herein in its entirety. Other exemplary retaining or locking mechanisms include, by way of non-limiting example, locking washers, locking screws, and bone screw covers. One skilled in the art will appreciate that various combinations of locking mechanisms can be used as well. Other exemplary locking mechanisms are disclosed in U.S. Pat. No. 6,331,179 to Fried et al., U.S. Pat. No. 6,159,213 to Rogozinski; U.S. Pat. No. 6,017,345 to Richelsoph; U.S. Pat. No. 5,676,666 to Oxiand et al.; U.S. Pat. No. 5,616,144 to Yapp et al.; U.S. Pat. No. 5,261,910 to Warden et al.; and U.S. Pat. No. 4,696,290 to Steffee.

It is understood that the bone plate system may include different types of bone screws having varying functionalities. For example, the bone screws can be of a rigid type in which after a screw locking mechanism is engaged, movement of the screw in any direction is prevented. The bone screws can also be of a semi-rigid type in which after a screw locking mechanism is engaged, screw backout is prevented, but the screw is able to move in all directions (i.e., polyaxially). Further, the bone screws can also be of a hybrid type in which after a screw locking mechanism is engaged, screw backout is prevented, but the screw is able to move in only one selected direction (e.g., the superior-inferior or the transverse direction). Moreover, the bone screws may translate within an aperture of a plate. For example, a bone screw may translate along the length of an elongated slot defining an aperture in the plate. One skilled in the art will appreciate that a bone plate system may be provided having any single screw type or a combination of all or any of the screw types.

Figure 9A:
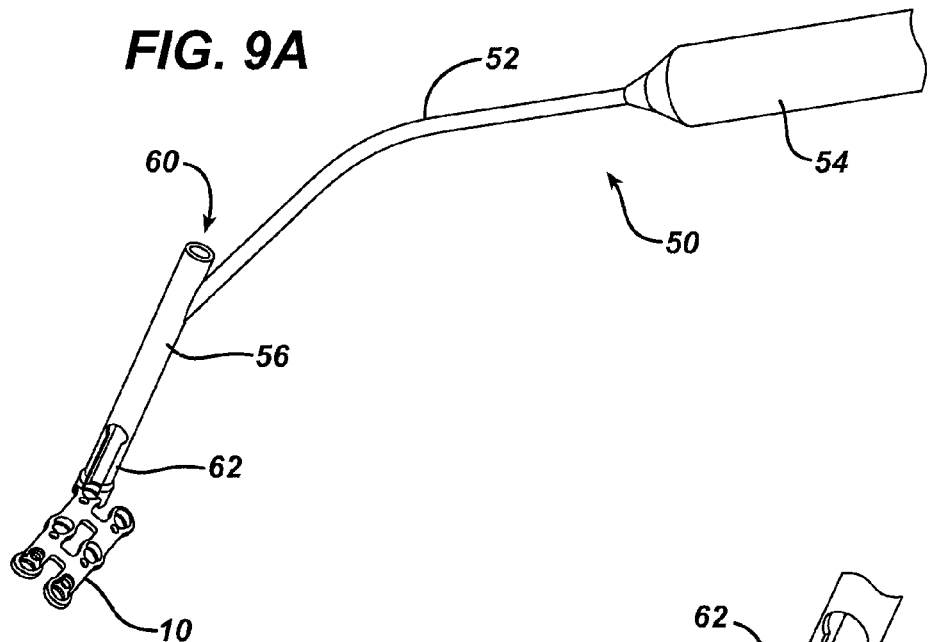
FIG. 9A is a perspective view of a guide device mated with the bone plate disclosed herein.
Figure 9B:
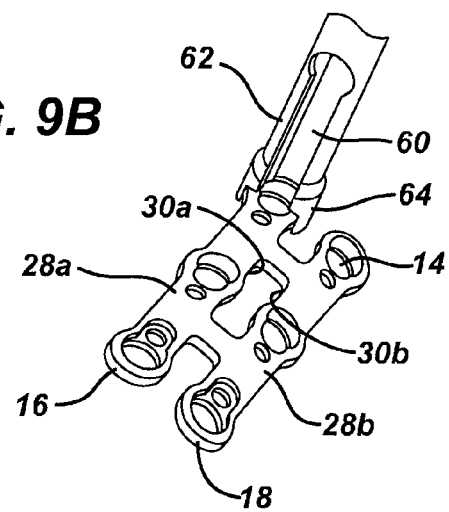
FIG. 9B is a detailed view of a portion of the guide device and bone plate of FIG. 9A.

The bone plate system can also include a surgical tool such as, for example, a guide device 50 adapted to mate with bone plate 10 in registration with bone screw holes 14. An exemplary guide device 50 is shown in FIGS. 9A and 9B. Guide device 50 generally includes an elongate shaft 52 having a proximal handle portion 54 and a distal end coupled to a guide member 56. The shaft 52 may be offset from, and angled with respect to, guide member 56, as shown in FIG. 9A. Guide member 56 includes a least one pathway 60 extending therethrough with one or more alignment members 62 extending from a distal portion thereof. Alignment members 62 can be spaced apart such that they are adapted to engage and/or align with a portion of the bone plate adjacent to and external of bone screw holes 14.

In one embodiment, pathway 60 is sized (i.e., in diameter) and shaped to allow the passage of a variety of bone preparation surgical tools (e.g., drill, tap, etc.) and bone screws 12 through pathway 60 and into bone beneath bone plate 10. In use, alignment members 62 are positioned external to bone screw hole 14 to position pathway 60 in registration with a bone screw hole. Once registration is achieved, the bone beneath bone plate 10 can be prepared (e.g., drilling, tapping, etc.), and bone screws subsequently can be implanted into the prepared bone through pathway 60 without removing guide device 50.

Alignment elements 62 can include two laterally opposed tabs 64 (FIG. 9B) adapted to engage the inner and outer sidewalls of rails 16, 18 adjacent to the bone screw holes. The tabs can be shaped to match the curved profile of the sidewalls adjacent to the bone screw holes. For example, a guide device adapted to register with the bone screw holes in the plate illustrated in FIGS. 2 and 3 would have symmetrical tabs 64, in which each tab is curved to match the curved profile of the sidewall of the plate adjacent to the bone screw holes. In another embodiment, a guide device adapted to register with the bone screw holes in the plate illustrated in FIGS. 4 though 6 would have asymmetrical tabs 64 in which one tab would be curved and another tab would be substantially linear to register with the complementarily shaped sidewalls of the plate adjacent to the bone screw holes. In one aspect, the relative dimensions of the space between tabs 64 and the width of the plate adjacent bone screw holes can be such that guide device 50 achieves an interference fit with one of rails 16, 18. Such an interference fit would enable the guide device 50 to engage the plate in a manner that enables it to function as a plate holder. One skilled in the art will appreciate the shape and spacing of tabs 64 can also be adapted to form a variety of other fits with bone plate 10, such as a sliding clearance fit.

Figure 9C:
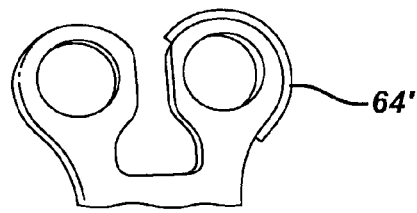
FIG. 9C is a bottom view of a portion of the bone plate showing a distal end of an arc shaped tab of a guide device positioned there around in accordance with another embodiment.

In one embodiment, guide device 50 is a single barrel device adapted to register with a single bone screw hole and having a single pathway 60 through the guide member 56 as shown in FIGS. 9A and 9B. One advantage of a single barrel guide device is that it enables a surgeon to adjust the trajectory of surgical instruments and bone screws inserted through pathway 60 while guide device 50 is in registration with bone screw hole 14. Tabs 64 on guide device 50 can mate the guide device to bone plate 10 with pathway 60 in registration bone screw hole 14 and pivot on bone plate 10. For example, tabs 64 can mate with a generally spherically shaped portion of the plate (i.e., top surface and/or sidewalls) and pivot upon this surface to achieve a desired trajectory. In a further embodiment, shown in FIG. 9C the guide device has a single tab 64' that extends over an arc of greater than 180°.

In another embodiment, a guide device could include multiple pathways for registering with multiple bone screw holes 14 at the same time. For example, the multiple pathways can be spaced such that when the guide device is mated to bone plate 10, the pathways register with two or more bone screw holes 14. One such exemplary guide device is disclosed in application Ser. No. 10/776,414, entitled "Guide For Spinal Tools, Implants, and Devices," filed Feb. 11, 2004 and incorporated hereby reference in its entirety. The alignment elements on the dual pathway guide device can similarly include two tabs that extend from the distal portion of the guide member. In use, the tabs can mate with the outer sidewall 28a, 28b of rails 16, 18 and span opposed bone screw holes.

Figure 10A:
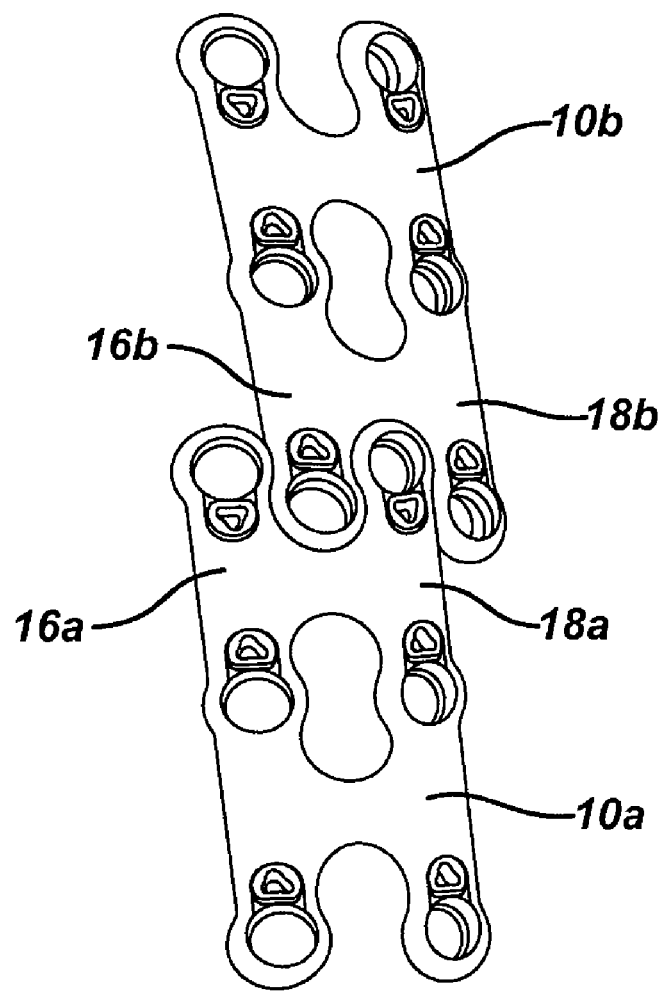
FIG. 10A is a perspective view of two bone plates encompassed by the invention positioned in a nesting configuration.

In an alternative embodiment of the bone plate system, multiple bone plates are provided. The bone plates can, for example, be adapted to work together and implanted in a nesting configuration as shown in FIG. 10A. The nesting configuration allows an overlap of the bone plates 10a, 10b on a single vertebral body to provide more rigid support to the spinal column when multiple plates are utilized. FIG. 10A illustrates two bone plates 10a, 10b in an exemplary nesting configuration. The first and a second bone plates 10a, 10b each include first and second longitudinally extending rails 16a, 16b and 18a, 18b wherein one of the first and second longitudinal rails 16a, 18a of the first bone plate 10a can be implanted between first and second longitudinally extending rails 16b, 18b of the second bone plate 10b.

Figure 10B:
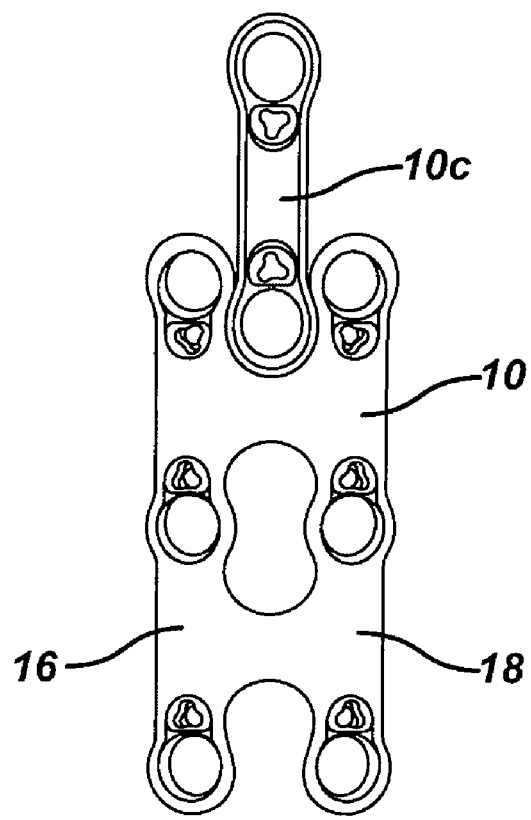
FIG. 10B is a top view of the bone plate encompassed by the invention positioned in a nesting configuration with a single rail bone plate.

The bone plate described herein can also be implanted in a nesting configuration with one or more of a variety of other bone plates, such as, for example another plate of the type described herein, or a plate in the form of a single rail with a single row of bone screw holes. One such exemplary single rail plate is described in the U.S. patent application entitled "Spinal Plate System and Method of Use," filed Nov. 16, 2004, and incorporated herein by reference in its entirety. FIG. 10B illustrates plate 10 in a nesting configuration with single rail bone plate 10c positioned between first and second longitudinally extending rails 16, 18.

Plate nesting configurations can be useful, for example, in a subsequent revision surgery, where it is useful to provide additional stability and fixation to a spinal column and/or to fortify previously implanted plates. The configuration of plate 10 is particularly advantageous for use in revision surgery because of the ability of plate 10 to nest with other plates. Bone plate 10 provides maximum stability while minimizing the space required to implant two (or more) plates on a single vertebral body.

During a revision procedure, a surgeon can implant the bone plate 10a such that it nests with a previously implanted double rail plate 10b as shown in FIG. 10A. The present system provides enhanced versatility in the event that revision surgery is required. The original plate can be a double rail plate that is augmented with another double rail plate (FIG. 10A) or with a single rail plate (FIG. 10B). It is understood that the original plate can be virtually any type of plate including a double rail plate or a single rail plate of the type shown in FIGS. 10A and 10B, which can be aligned with a nesting plate that is, for example, a double rail plate or a single rail plate.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A single barrel guide device, comprising:
  a guide barrel portion adapted to register with a single bone screw hole; and
  a pair of adjacent features extending from a distal end of the guide barrel, the pair of adjacent features being adapted to enable the guide barrel to register with a single bone screw hole on a bone plate such that the adjacent features engage portions of the bone plate located on opposed sides of the bone screw hole adjacent to and external to the bone screw hole such that the guide barrel is adapted to receive and guide an instrument through the bone screw hole while the guide barrel is in registration with the bone screw hole.

2. The single barrel guide device of claim 1, wherein the pair of adjacent features are tabs adapted to contact an outer side surface of a bone plate.

3. The single barrel guide device of claim 1, wherein the guide barrel portion is adapted to receive and guide an implant.

4. The single barrel guide device of claim 1, further including a handle, attached to a portion of the guide barrel.

5. A single barrel guide device, comprising:
  a guide barrel portion adapted to register with a single bone screw hole; and
  a tab extending from a distal end of the guide barrel, the tab being adapted to enable the guide barrel to register with a single bone screw hole on a bone plate such that the tab engages a curved portion of the bone plate adjacent to and external to the bone screw hole such that the guide barrel is adapted to receive and guide an instrument through the bone screw hole while the guide barrel is in registration with the bone screw hole,
  wherein the tab approximates an arc of at least approximately 180 degrees such that the tab is adapted to be positioned against and to engage a sidewall of a bone plate that has complementary arc-shaped configuration.

* * * * *